(12) United States Patent
Kotlyar et al.

(10) Patent No.: US 6,893,618 B2
(45) Date of Patent: May 17, 2005

(54) DEVICE FOR AIR CLEANING FROM DUST AND AEROSOLS

(76) Inventors: Gennady Mikhailovich Kotlyar, Kv. 52, d.51, ul Polesskaya, Orel 302028 (RU); Ivan Vasilievich Sysoev, Kv. 195, d. 55, ul., Polesskaya Orel 302028 (RU)

( * ) Notice: Subject to any disclaimer, the term of this patent is extended or adjusted under 35 U.S.C. 154(b) by 117 days.

(21) Appl. No.: 10/065,824

(22) Filed: Nov. 22, 2002

(65) Prior Publication Data

US 2004/0052700 A1 Mar. 18, 2004

(30) Foreign Application Priority Data

Mar. 27, 2001 (RU) ........................................ 2001107867

(51) Int. Cl.$^7$ .............................................. B01J 19/08
(52) U.S. Cl. .......................... 422/186.04; 422/186.21; 422/186.07; 422/186.13; 422/186.26
(58) Field of Search ....................... 422/186.04, 186.21, 422/186.07, 186.13, 186.26

(56) References Cited

U.S. PATENT DOCUMENTS

| | | | |
|---|---|---|---|
| 3,841,840 A | 10/1974 | Hundhausen et al. | .......... 23/284 |
| 5,215,558 A | * 6/1993 | Moon | ............................ 96/62 |
| 5,468,454 A | 11/1995 | Kim | ........................... 422/121 |
| 5,601,791 A | * 2/1997 | Plaks et al. | ................. 422/169 |
| 6,364,941 B2 | * 4/2002 | Liu et al. | ........................ 96/60 |

* cited by examiner

*Primary Examiner*—Steven Versteeg
(74) *Attorney, Agent, or Firm*—Anton J. Hopen; Smith & Hopen, P.A.

(57) ABSTRACT

A device for air cleaning from dust and aerosols based on the use of non-homogeneous electrostatic field creating a flow of charged particles (the so called "ionic wind") and operating as electrostatic precipitator. The device comprises a body inside which corona-forming and precipitation electrodes with opposite polarities are established. Inside the body deflection electrodes are established as well, in front of corona-forming electrodes a reflector for positively charged aeroions by an electrode electrically coupled with said corona-forming electrodes being established. The device comprises one or several tapes made of porous-fiber material placed into non-homogeneous electric field.

5 Claims, 2 Drawing Sheets

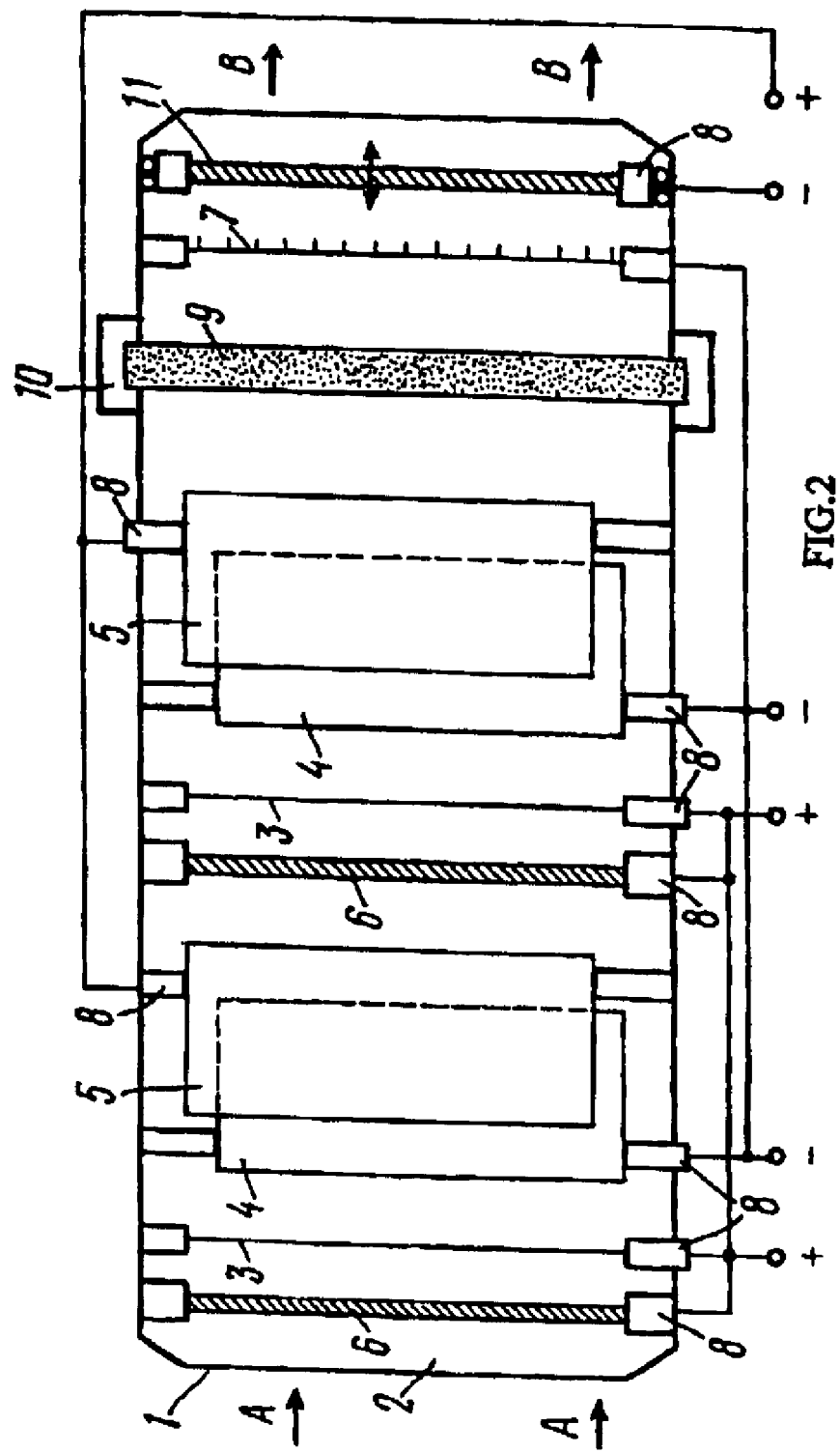

000
DEVICE FOR AIR CLEANING FROM DUST AND AEROSOLS

CROSS-REFERENCE TO RELATED DISCLOSURE

The present application is a U.S. National Stage application claiming the benefit of prior filed International Application, serial number PCT/RU01/00247, filed Jun. 21, 2001, which International Application claims a priority date of Mar. 27, 2001 based on prior filed Russian Application serial number RU2001/107867.

TECHNICAL FIELD

The present invention relates to separation of disperse particles with the use of an electrostatic effect, to be more precise, the present invention relates to devices aimed at cleaning dust and aerosols from the air. The invention has applications in all fields of industry as well as in domestic rooms.

BACKGROUND ART

One device contained in the prior art comprises a body with an air inlet and corona-forming and precipitation electrodes of opposite polarities. An electrostatic precipitation element is installed near the precipitation electrodes. The electrostatic precipitation element comprises two metal nets with precipitating fabric set in-between (for ref. see Inventor's Certificate of the USSR No. 921629, class B 03 C 3/08).

The above-mentioned known device does not avoid extraction of harmful positively charged aeroions. Additionally, the system does not provide for saturation of cleaned air with molecules of aromatic or medical substances if necessary.

As to its principle of operation, the proposed device is closest to a device described in the Patent of Russian Federation No. 2159683, class B C 3/04 published in 2000. This known device comprises a body with an air inlet. Located inside the body are corona-forming and precipitation electrodes with opposite polarities, passive electrodes are set, behind electrodes an electrode—generator of negative electrodes being electrically coupled with precipitation electrodes and a vessel with aroma or medical substances are mounted.

The principle upon which the prior art device is based is the forming of charged particles in the field of corona-forming charge appearing between positively charged corona and negatively charged precipitation electrodes. Corona-forming and deflecting electrodes have similar polarities but different electrical potential in relation to precipitation electrodes. The presence of deflection electrodes increases level of purification of air greatly (up to 95–99 percent). Passive electrode acquiring positive charge prevents positively charged aeroions from leaving air cleaner thus preventing an environment from being polluted with harmful positively charged aeroions. Said air cleaner provides for the forming of negatively charged aeroions of oxygen in great quantities. A portion of these ions are seized by dust or aerosol particles and then fall on passive electrodes thus covering electrodes with a dielectric fine dispersion layer. This layer of dust partially neutralizes positively charged electrodes but mainly decreases the efficiency of the passive electrode as a precipitator of positively charged aeroions. Therefore, it becomes necessary to clean the passive electrodes, thus creating additional work and inconvenience.

The use of a vessel allows saturation of the air with aromatic substances; however, liquid overflowing from the vessel is mixed with dust which has fallen. This situation makes the inner surfaces dirty, worsens electric isolation, safety and may produce electrical failure. Likewise, the intensity of liquid evaporation in a non-homogeneous electric field is relatively great, small amounts of liquid are evaporated very fast. This requires frequent refilling of the vessel with aromatic or medical liquids. As the vessel is mounted inside the air cleaner, such recharges are connected, as a rule, with partial or full reassembling of the device which leads to additional time and inconvenience. High aerodynamic resistance also reduces efficiency of the device.

SUMMARY OF THE INVENTION

One advantage of the present invention is a device which purifies air by removing dust and aerosols.

Another advantage of the present invention is the ability to saturate the air with aromatic and medical substances.

Still another advantage of the present invention is its ease of use and greater application for complex air treatment.

These advantages are incorporated in a device for air purification by removing dust and aerosols comprising a body with an air inlet, disposed inside said body are corona and collecting electrodes having opposite polarities, deflecting electrodes behind which an electrode-generator of negatively charged electrons is mounted. Said generator is electrically coupled with precipitation electrodes. In the body a vessel for holding aromatic and medical substances is mounted. A reflector of positively charged electrons is mounted in front of the corona forming electrode. The reflector is electrically coupled with the corona-forming electrodes, while the means for distributing aromatic or medical substances includes one or more tapes made of porously-fiber material whose ends are placed within the vessel containing the aroma or medical substances being mounted beyond the body.

The proposed device allows for the removal of harmful positively charged aeroions. Additionally, it is not necessary to clean any dust from the reflector. Direct measurements have shown that concentrations of positively charged aeroions at the inlet are decreased to tens of thousand, as well as the background values of positively charged aeroions concentrations at inlet of the device. This can be explained by the fact that the positively charged reflector pushes away aeroions from the inlet of the air cleaner. While in operation, dielectric fine dispersion dust is collected on the reflector, nevertheless this fact does not lessen its efficiency, as it constantly remains under a high positive potential. A layer of dielectric fine dispersion dust does not influence the dispersion of power of the electrostatic field of a reflector. Thus, cleaning of the reflector is not necessary and it can be combined with the cleaning of precipitation and deflecting electrodes if necessary.

Rather than relying on a vessel to hold aromatic or medicinal substances, a wick-like tape made of porously-fiber material is used. The tapes reduce aerodynamic resistance to air flow greatly as the thickness of the tape is not more than several millimeters. Additionally, problems associated with water or condensation coming in contact with the deflection electrodes is avoided. As the vessels for liquids are placed beyond operation zone of the device, refilling of the vessels can be performed through special aperture by means of syringe or other known method without switching the device off the power source. There are no restrictions regarding the present invention's capacity for aromatic or medical substances. A plurality of tapes can be used rather than relying on a single wick-like tape.

The present invention may also be used as ozonizer. This is accomplished by distancing the accelerating electrode (positively charged) from the electrode generator. The device is constructed so that the position of the accelerating electrode is adjustable in relation to electrode generator. A high-frequency alternating current is provided to accelerating electrode.

To increase productivity and to raise the coefficient of purification of air by removing dust and aerosols, a plurality of reflectors of positively charged aeroions, corona-forming, precipitation and deflection electrodes are placed in sequence.

BRIEF DESCRIPTION OF DRAWINGS

The present invention will now be described in greater detail with reference to various specific embodiments thereof taken in conjunction with the accompanying drawings, in which:

FIG. 2 illustrates one of the embodiments of the proposed device.

DETAILED DESCRIPTION OF THE PREFERRED EMBODIMENTS

Figure 1:
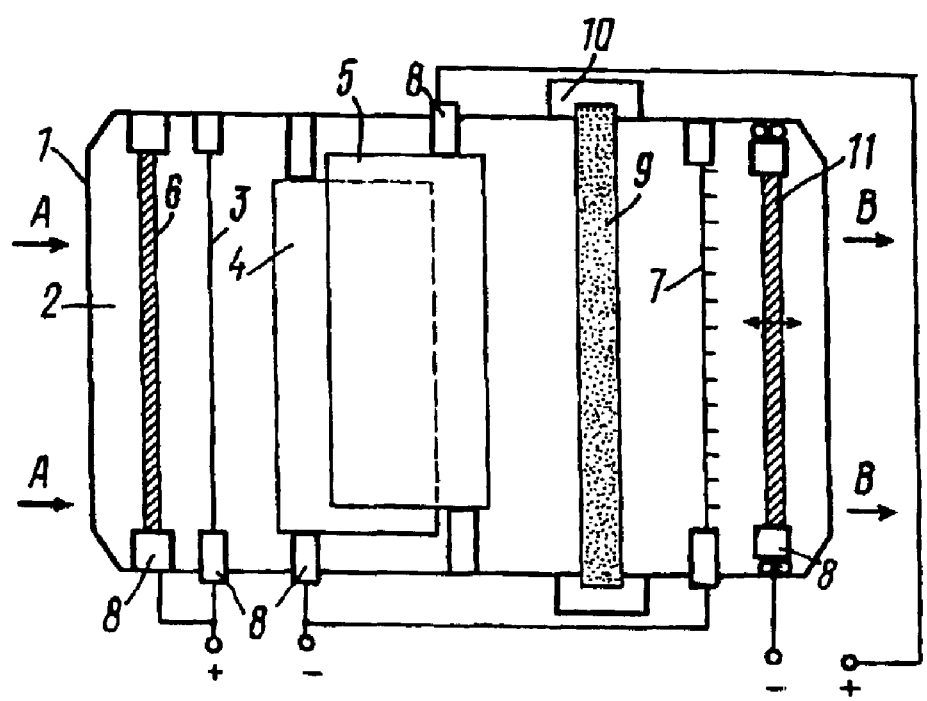
FIG. 1 illustrates a general embodiment of the proposed device.

The proposed device comprises a body 1 (FIG. 1) with valve 2 for air, said valve having inlet and outlet (not shown in FIG. 1). Air enters the device through valve 2, shown in FIG. 1 by means of "A" arrow, while air output is shown by means of "B" arrow. Inside the body corona-forming electrodes 3 (positively charged) and precipitation electrodes 4 (negatively charged), as well as deflecting electrodes 5 (positively charged). Voltage volume supplied to the deflecting electrode 5 is less than voltage volume supplied to the corona-forming electrodes 3 and precipitation electrodes 4. In front of, and parallel to, corona-forming electrodes 3, a reflector of positively charged aeroions is placed at a distance. The reflector includes electrodes 6 electrically coupled with electrodes 3, electrodes 6 having bigger diameter than that of electrodes 3.

Behind deflection electrodes 5 an electrode-generator 7 of negatively charged aeroions is established, being electrically coupled with precipitation electrodes 4. The electrode-generator 7 may comprise an electro-conducting net made of thin wire and may be equipped with concentrators comprised of needles.

Corona-forming electrodes 3 in this particular embodiment are constructed as thin electricity conducting threads made of tungsten wire of a relative diameter. Reflector-electrodes 6 are constructed as rods made of stainless steel of round-section with a diameter about 10–20 times greater than that of electrodes 3. Precipitation electrodes 4 and deflection electrodes 5 are constructed as electricity conducting plates. All electrodes are disposed within body 1, made of a dielectric material, on electricity insulators 8.

One, or several, wick-like tapes 9, made of porously-fiber material whose ends are placed in vessels 10 containing aromatic or medical substances, can be placed in front of electrode 7. Tapes 9 are placed in the zone of the most-homogeneous electric field—i.e., between deflection electrodes 5 and electrode—generator 7 of negatively charged aeroions.

To use the device as an ozonizer, an accelerating electrode 11 is placed at a distance behind electrode-generator 7, a controlled positive potential is supplied to the electrode 11, a controlled non-homogeneous electric field is formed between electrode-generator 7 and accelerating electrode 11. Change in volume and gradient of the field is achieved by means of either change of voltage volume between electrodes 7 and 11, or change of a distance between the electrodes due to replacement of electrode 11 in respect to electrode-generator 7.

To increase the productivity of ozone, change of corona-forming 3, precipitation 4 and deflection 5 electrodes' polarities is provided. Instead of direct current, a high frequency alternative current (50 kHz and up) may be supplied to electrodes 7 and 11 thus increasing volume of ozone produced.

FIG. 2 represents one embodiment wherein the efficiency of cleaning dust and aerosols from the air is achieved.

In this embodiment several reflectors 6 of positively charged aeroions, several corona forming 3, precipitation 4 and deflection 5 electrodes are used.

Under supply of high voltage to corona-forming 3 and precipitation 4 electrodes a corona discharge is created, thus forming a flow of positively charged nitrogen and oxygen ions directed toward precipitation electrodes 4. This effect is called "ionic wind." Together with aeroions in the non-homogeneous electric field neutral molecules, as well as particles of dust and aerosols, contained in the air and moving towards precipitation electrodes are polarized and charged. Particles of dust and aerosol, after being positively charged, are dropped to precipitation electrodes 4 while negatively charged particles are dropped to deflection electrodes 5. In addition the particles produce a slowing effect upon positively charged particles which, due to their high velocity, can not be dropped to precipitation electrodes. Due to this, deflection electrodes 5 level of purification reaches 95–99 percent. The electric field of reflector 6 has positive potential thus preventing harmful positively charged aeroions from leaving the device; it changes the direction of their movement to the opposite one thus directing particles towards precipitation electrodes 4 thus increasing air purity. Corona-forming electrodes 7 disposed behind deflection electrodes 5 saturate the air with negatively charged aeroions of oxygen. Positively charged aeroions, having passed through slowing-down field of deflection electrode 5, are changed upon entering the zone filled with negatively charged aeroions of oxygen and electrons. In this case, the concentration of positively charged aeroions at the outlet is reduced considerately to their background level while concentration of useful negatively charged aeroions increases greatly. Direct measurements prove that in this particular case ozone is almost absent.

During ozonization negative potential is supplied to corona-forming electrodes 3, positive potential is supplied to precipitation electrodes 4, while deflection electrodes 5 are supplied with negative potential of less value. To increase the amount of ozone produced electrodes 7 and 11 are supplied with high voltage, whose volume can be changed, thus, allowing control of ozone production in a wide range. It is noticeable that the efficiency of air cleaning from dust and aerosols under this particular rate is not lower than that in conditions of positive corona-forming while the amount of negatively charged oxygen aeroions is much greater.

Aromatic or medical substances are transferred through tape 9 made of porously-fiber material from vessels 10 to the zone of non-homogeneous electricity field under forces of inter-molecular interaction (known as capillary phenomenon). In the non-homogeneous field additionally Koulon forces are applied to polarized molecules of liquid, the forces are directed toward the raise in tension of electrical field. These forces reduce attraction between molecules thus promoting faster evaporation of aromatic or medical substances. Control over the intense of evaporation of liquid is provided by the fact that open (free) surface of liquid in the tape of porously-fiber material may be controlled in wide range. By means of cleaned air flow molecules of aromatic or medical substances together with negatively charged aeroions of oxygen are taken beyond air cleaner. Both the method described and the device proposed do not require any dissolvent polluting environment, as well as special sprays, inhalators and fans. While ozonization air saturation with aromatic or medical substances is not recommended as non-controlled oxidation of the substances by means of ozone may take place.

INDUSTRIAL APPLICABILITY

The proposed device has applications both in industrial and domestic capacities for saturation of air with molecules with aromatic and medical substances, negatively charged oxygen aeroions as well as with controlled amount of ozone.

What is claimed is:

1. A device for air cleaning from dust and aerosols comprising: a body with an air inlet, inside the body corona-forming and precipitation electrodes with opposite polarities, deflection electrodes are established, behind said deflection electrodes electrode-generator of negatively charged aeroions is established being electrically coupled with precipitation electrodes as well as a means for aromatic or medical substances wherein in front of corona-forming electrodes a reflector of positively charged aeroions is established being electrically coupled with said corona-forming electrodes, while a means for aromatic or medical substances is effected as one or several tapes made of porously-fiber material, which ends are placed in capacities containing aromatic or medical substances, said capacities are places beyond the body of the device.

2. A device according to claim 1 wherein behind electrode-generator at a distance an accelerating electrode is established, to which a controlled positive potential is supplied.

3. A device according to claim 2 wherein accelerating electrode is effected with a possibility of movement in respect to electrode-generator.

4. A device according to claim 2 wherein a high-frequency alternating current is supplied to electrode-generator.

5. A device according to any of claim 4 further comprising several reflectors of positively charged aeroions, corona-forming, precipitation and deflection electrodes places in sequence.

* * * * *